United States Patent
Chen (10) Patent No.: US 10,156,541 B2
(45) Date of Patent: *Dec. 18, 2018

(54) SYSTEM FOR DETECTING ELECTRICAL PROPERTIES OF A MOLECULAR COMPLEX

(71) Applicant: Genia Technologies, Inc., Santa Clara, CA (US)

(72) Inventor: Roger J. A. Chen, Saratoga, CA (US)

(73) Assignee: Genia Technologies, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/819,994

(22) Filed: Nov. 21, 2017

(65) Prior Publication Data

US 2018/0100827 A1  Apr. 12, 2018

Related U.S. Application Data

(63) Continuation of application No. 14/558,268, filed on Dec. 2, 2014, now Pat. No. 9,869,655, which is a
(Continued)

(51) Int. Cl.
*G01N 27/327* (2006.01)
*G01N 33/487* (2006.01)
(Continued)

(52) U.S. Cl.
CPC ....... *G01N 27/3278* (2013.01); *C12Q 1/6874* (2013.01); *G01N 27/44791* (2013.01); *G01N 33/48721* (2013.01)

(58) Field of Classification Search
None
See application file for complete search history.

(56) References Cited

U.S. PATENT DOCUMENTS

| 2,656,508 A | 10/1953 | Coulter |
| 3,638,120 A | 1/1972 | Jost |
(Continued)

FOREIGN PATENT DOCUMENTS

| CN | 101421616 | 4/2009 |
| CN | 103193189 | 7/2013 |
(Continued)

OTHER PUBLICATIONS

Akeson, et al. Microsecond time-scale discrimination among polycytidylic acid, polyadenylic acid, and plolyuridylic acid as homopolymers or a s segments within single RNA molecules. Biophys J. Dec. 1999; 77(6):3227-33.
(Continued)

*Primary Examiner* — Robert T. Crow
(74) *Attorney, Agent, or Firm* — Van Pelt, Yi & James LLP (57) ABSTRACT

A system for detecting electrical properties of a molecular complex is disclosed. The system includes an electrode electrically coupled to a molecular complex that outputs an electrical signal affected by an electrical property of the molecular complex, wherein the effect of the electrical property of the molecular complex on the electrical signal is characterized by an expected bandwidth. The system further includes an integrating amplifier circuit configured to receive the electrical signal from the electrode. The integrating amplifier circuit is further configured to selectively amplify and integrate a portion of the electrical signal over time within a predetermined bandwidth, wherein the predetermined bandwidth is selected at least in part based on the expected bandwidth.

12 Claims, 6 Drawing Sheets

Related U.S. Application Data continuation of application No. 13/272,128, filed on Oct. 12, 2011, now Pat. No. 8,962,242.

(60) Provisional application No. 61/435,700, filed on Jan. 24, 2011.

(51) Int. Cl.
  *C12Q 1/6874* (2018.01)
  *G01N 27/447* (2006.01)

(56) References Cited

U.S. PATENT DOCUMENTS

| | | | |
|---|---|---|---|
| 4,121,192 A | 10/1978 | Wilson | |
| 4,713,347 A | 12/1987 | Mitchell | |
| 4,859,945 A | 8/1989 | Stokar | |
| 5,021,692 A | 6/1991 | Hughes | |
| 5,198,543 A | 3/1993 | Blanco | |
| 5,235,267 A | 8/1993 | Schoneberg | |
| 5,260,663 A | 11/1993 | Blades | |
| 5,302,509 A | 4/1994 | Cheeseman | |
| 5,308,539 A | 5/1994 | Koden | |
| 5,457,342 A | 10/1995 | Herbst, II | |
| 5,541,851 A | 7/1996 | Sato | |
| 5,569,950 A | 10/1996 | Lewis | |
| 5,576,204 A | 11/1996 | Blanco | |
| 5,747,805 A | 5/1998 | Youngquist | |
| 5,756,355 A | 5/1998 | Lang | |
| 5,770,367 A | 6/1998 | Southern | |
| 5,795,782 A | 8/1998 | Church | |
| 5,804,386 A | 9/1998 | Ju | |
| 5,814,454 A | 9/1998 | Ju | |
| 5,869,244 A | 2/1999 | Martin | |
| 5,876,936 A | 3/1999 | Ju | |
| 5,912,155 A | 6/1999 | Chatterjee | |
| 5,939,301 A | 8/1999 | Hughes, Jr. | |
| 5,952,180 A | 9/1999 | Ju | |
| 5,981,733 A | 11/1999 | Gamble | |
| 6,012,291 A | 1/2000 | Ema | |
| 6,014,213 A | 1/2000 | Waterhouse | |
| 6,015,714 A | 1/2000 | Baldarelli | |
| 6,046,005 A | 4/2000 | Ju | |
| 6,082,115 A | 7/2000 | Strnad | |
| 6,210,896 B1 | 4/2001 | Chan | |
| 6,217,731 B1 | 4/2001 | Kane | |
| 6,232,103 B1 | 5/2001 | Short | |
| 6,255,083 B1 | 7/2001 | Williams | |
| 6,261,797 B1 | 7/2001 | Sorge | |
| 6,265,193 B1 | 7/2001 | Brandis | |
| 6,321,101 B1 | 11/2001 | Holmström | |
| 6,362,002 B1 | 3/2002 | Denison | |
| 6,383,749 B2 | 5/2002 | Bochkariov | |
| 6,399,320 B1 | 6/2002 | Markau | |
| 6,399,335 B1 | 6/2002 | Kao | |
| 6,413,792 B1 | 7/2002 | Sauer | |
| 6,485,703 B1 | 11/2002 | Cote | |
| 6,607,883 B1 | 8/2003 | Frey | |
| 6,616,895 B2 | 9/2003 | Dugas | |
| 6,627,748 B1 | 9/2003 | Ju | |
| 6,664,079 B2 | 12/2003 | Ju | |
| 6,673,615 B2 | 1/2004 | Denison | |
| 6,686,997 B1 | 2/2004 | Allen | |
| 6,699,719 B2 | 3/2004 | Yamazaki | |
| 6,723,513 B2 | 4/2004 | Lexow | |
| 6,746,594 B2 | 6/2004 | Akeson | |
| 6,762,048 B2 | 7/2004 | Williams | |
| 6,794,177 B2 | 9/2004 | Markau | |
| 6,800,933 B1 | 10/2004 | Mathews | |
| 6,824,659 B2 | 11/2004 | Bayley | |
| 6,880,346 B1 | 4/2005 | Tseng | |
| 6,891,278 B2 | 5/2005 | Muller | |
| 6,916,665 B2 | 7/2005 | Bayley | |
| 6,952,651 B2 | 10/2005 | Su | |
| 7,033,762 B2 | 4/2006 | Nelson | |
| 7,041,812 B2 | 5/2006 | Kumar | |
| 7,052,839 B2 | 5/2006 | Nelson | |
| 7,057,026 B2 | 6/2006 | Barnes | |
| 7,074,597 B2 | 7/2006 | Ju | |
| 7,153,672 B1 | 12/2006 | Eickbush | |
| 7,189,503 B2 | 3/2007 | Akeson | |
| 7,223,541 B2 | 5/2007 | Fuller | |
| 7,229,799 B2 | 6/2007 | Williams | |
| 7,238,485 B2 | 7/2007 | Akeson | |
| 7,244,602 B2 | 7/2007 | Frey | |
| 7,279,337 B2 | 10/2007 | Zhu | |
| 7,321,329 B2 | 1/2008 | Tooyama | |
| 7,368,668 B2 | 5/2008 | Ren | |
| 7,405,281 B2 | 7/2008 | Xu | |
| 7,410,564 B2 | 8/2008 | Flory | |
| 7,446,017 B2 | 11/2008 | Liu | |
| 7,452,698 B2 | 11/2008 | Sood | |
| 7,468,271 B2 | 12/2008 | Golovchenko | |
| 7,572,624 B2 | 8/2009 | Gumbrecht | |
| 7,622,934 B2 | 11/2009 | Hibbs | |
| 7,625,701 B2 | 12/2009 | Williams | |
| 7,626,379 B2 | 12/2009 | Peters | |
| 7,710,479 B2 | 5/2010 | Nitta | |
| 7,727,722 B2 | 6/2010 | Nelson | |
| 7,745,116 B2 | 6/2010 | Williams | |
| 7,777,013 B2 | 8/2010 | Xu | |
| 7,777,505 B2 | 8/2010 | White | |
| 7,871,777 B2 | 1/2011 | Schneider | |
| 7,897,738 B2 | 3/2011 | Brandis | |
| 7,906,371 B2 | 3/2011 | Kim | |
| 7,924,335 B2 | 4/2011 | Itakura | |
| 7,939,259 B2 | 5/2011 | Kokoris | |
| 7,939,270 B2 | 5/2011 | Holden | |
| 7,947,454 B2 | 5/2011 | Akeson | |
| 7,948,015 B2 | 5/2011 | Rothberg | |
| 7,973,146 B2 | 7/2011 | Shen | |
| 7,989,928 B2 | 8/2011 | Liao | |
| 8,022,511 B2 | 9/2011 | Chiu | |
| 8,058,030 B2 | 11/2011 | Smith | |
| 8,058,031 B2 | 11/2011 | Xu | |
| 8,133,672 B2 | 3/2012 | Bjornson | |
| 8,137,569 B2 | 3/2012 | Harnack | |
| 8,148,516 B2 | 4/2012 | Williams | |
| 8,192,961 B2 | 6/2012 | Williams | |
| 8,252,911 B2 | 8/2012 | Bjornson | |
| 8,257,954 B2 | 9/2012 | Clark | |
| 8,324,914 B2 | 12/2012 | Chen | |
| 8,461,854 B2 | 6/2013 | Chen | |
| 8,828,208 B2 | 9/2014 | Canas | |
| 8,962,242 B2 | 2/2015 | Chen | |
| 9,581,563 B2 | 2/2017 | Chen | |
| 9,605,307 B2 | 3/2017 | Chen | |
| 9,869,655 B2 * | 1/2018 | Chen | G01N 33/48721 |
| 2002/0039743 A1 | 4/2002 | Hashimoto | |
| 2003/0027140 A1 | 2/2003 | Ju | |
| 2003/0054360 A1 | 3/2003 | Gold | |
| 2003/0080042 A1 | 5/2003 | Barth | |
| 2003/0101006 A1 | 5/2003 | Mansky | |
| 2003/0102263 A1 | 6/2003 | Lopez | |
| 2003/0166282 A1 | 9/2003 | Brown | |
| 2003/0198982 A1 | 10/2003 | Seela | |
| 2004/0053337 A1 | 3/2004 | Yamazaki | |
| 2004/0122335 A1 | 6/2004 | Sackellares | |
| 2004/0144658 A1 | 7/2004 | Flory | |
| 2004/0185466 A1 | 9/2004 | Ju | |
| 2004/0262636 A1 | 12/2004 | Yang | |
| 2005/0032081 A1 | 2/2005 | Ju | |
| 2005/0091989 A1 | 5/2005 | Leija | |
| 2005/0127035 A1 | 6/2005 | Ling | |
| 2005/0136408 A1 | 6/2005 | Tom-Moy | |
| 2005/0164286 A1 | 7/2005 | O'uchi | |
| 2005/0186576 A1 | 8/2005 | Chan | |
| 2005/0208574 A1 | 9/2005 | Bayley | |
| 2005/0221351 A1 | 10/2005 | Ryu | |
| 2005/0239134 A1 | 10/2005 | Gorenstein | |
| 2006/0057565 A1 | 3/2006 | Ju | |
| 2006/0057585 A1 | 3/2006 | McAllister | |
| 2006/0105373 A1 | 5/2006 | Pourmand | |
| 2006/0105461 A1 | 5/2006 | Tom-Moy | |
| 2006/0246497 A1 | 11/2006 | Huang | |

(56) References Cited

U.S. PATENT DOCUMENTS

| | | |
|---|---|---|
| 2006/0252038 A1 | 11/2006 | Ju |
| 2006/0278992 A1 | 12/2006 | Trezza |
| 2007/0173731 A1 | 7/2007 | Meka |
| 2007/0190542 A1 | 8/2007 | Ling |
| 2007/0191015 A1 | 8/2007 | Hwang |
| 2007/0196846 A1 | 8/2007 | Hanzel |
| 2007/0275387 A1 | 11/2007 | Ju |
| 2008/0094076 A1 | 4/2008 | Hibbs |
| 2008/0101988 A1 | 5/2008 | Kang |
| 2008/0108082 A1 | 5/2008 | Rank |
| 2008/0171316 A1 | 7/2008 | Golovchenko |
| 2008/0199932 A1 | 8/2008 | Hanzel |
| 2008/0217546 A1 | 9/2008 | Steadman |
| 2008/0218184 A1 | 9/2008 | White |
| 2008/0254995 A1 | 10/2008 | Kim |
| 2008/0286768 A1 | 11/2008 | Lexow |
| 2008/0318245 A1 | 12/2008 | Smirnov |
| 2009/0029477 A1 | 1/2009 | Meller |
| 2009/0066315 A1 | 3/2009 | Hu |
| 2009/0073293 A1 | 3/2009 | Yaffe |
| 2009/0087834 A1 | 4/2009 | Lexow |
| 2009/0099786 A1 | 4/2009 | Oliver |
| 2009/0102534 A1 | 4/2009 | Schmid |
| 2009/0136958 A1 | 5/2009 | Gershow |
| 2009/0167288 A1 | 7/2009 | Reid |
| 2009/0215050 A1 | 8/2009 | Jenison |
| 2009/0233280 A1 | 9/2009 | Nomoto |
| 2009/0269759 A1 | 10/2009 | Menchen, Jr. |
| 2009/0298072 A1 | 12/2009 | Ju |
| 2010/0025238 A1 | 2/2010 | Gottlieb |
| 2010/0025249 A1 | 2/2010 | Polonsky |
| 2010/0035260 A1 | 2/2010 | Olasagasti |
| 2010/0047802 A1 | 2/2010 | Bjorson |
| 2010/0072080 A1 | 3/2010 | Karhanek |
| 2010/0075328 A1 | 3/2010 | Bjornson |
| 2010/0075332 A1 | 3/2010 | Patel |
| 2010/0078325 A1 | 4/2010 | Oliver |
| 2010/0078777 A1 | 4/2010 | Barth |
| 2010/0084276 A1 | 4/2010 | Lindsay |
| 2010/0092952 A1 | 4/2010 | Ju |
| 2010/0093555 A1 | 4/2010 | Bjornson |
| 2010/0121582 A1 | 5/2010 | Pan |
| 2010/0122907 A1 | 5/2010 | Stanford |
| 2010/0148126 A1 | 6/2010 | Guan |
| 2010/0196203 A1 | 8/2010 | Sanghera |
| 2010/0243449 A1 | 9/2010 | Oliver |
| 2010/0261247 A1 | 10/2010 | Hanzel |
| 2010/0261287 A1 | 10/2010 | Holt |
| 2010/0292101 A1 | 11/2010 | So |
| 2010/0297644 A1 | 11/2010 | Kokoris |
| 2010/0301398 A1 | 12/2010 | Rothberg |
| 2010/0320094 A1 | 12/2010 | White |
| 2010/0331194 A1 | 12/2010 | Turner |
| 2011/0005918 A1 | 1/2011 | Akeson |
| 2011/0008775 A1 | 1/2011 | Gao |
| 2011/0050200 A1 | 3/2011 | Tartagni |
| 2011/0053284 A1 | 3/2011 | Meller |
| 2011/0059505 A1 | 3/2011 | Hanzel |
| 2011/0165652 A1 | 7/2011 | Hardin |
| 2011/0168551 A1 | 7/2011 | White |
| 2011/0168968 A1 | 7/2011 | Yang |
| 2011/0174625 A1 | 7/2011 | Akeson |
| 2011/0189659 A1 | 8/2011 | Clark |
| 2011/0192723 A1 | 8/2011 | Chen |
| 2011/0193249 A1 | 8/2011 | Chen |
| 2011/0193570 A1 | 8/2011 | Chen |
| 2011/0218414 A1 | 9/2011 | Kamath |
| 2011/0226623 A1 | 9/2011 | Timp |
| 2011/0244447 A1 | 10/2011 | Korlach |
| 2011/0287414 A1 | 11/2011 | Chen |
| 2012/0034602 A1 | 2/2012 | Emig |
| 2012/0040343 A1 | 2/2012 | Timp |
| 2012/0040869 A1 | 2/2012 | Meller |
| 2012/0052188 A1 | 3/2012 | Chen |
| 2012/0094278 A1 | 4/2012 | Akeson |
| 2012/0094332 A1 | 4/2012 | Lee |
| 2012/0115736 A1 | 5/2012 | Bjornson |
| 2012/0133354 A1 | 5/2012 | Canas |
| 2012/0149021 A1 | 6/2012 | Yung |
| 2012/0160681 A1 | 6/2012 | Davis |
| 2012/0160687 A1 | 6/2012 | Akeson |
| 2012/0160688 A1 | 6/2012 | Davis |
| 2012/0187963 A1 | 7/2012 | Chen |
| 2012/0188092 A1 | 7/2012 | Chen |
| 2012/0196759 A1 | 8/2012 | Chen |
| 2012/0261261 A1 | 10/2012 | Huber |
| 2012/0322679 A1 | 12/2012 | Brown |
| 2013/0015068 A1 | 1/2013 | Chen |
| 2013/0071837 A1 | 3/2013 | Winters-Hilt |
| 2013/0118902 A1 | 5/2013 | Akeson |
| 2013/0207205 A1 | 8/2013 | Chen |
| 2013/0244340 A1 | 9/2013 | Davis |
| 2013/0263946 A1 | 10/2013 | Afzali-Ardakani |
| 2013/0327644 A1 | 12/2013 | Turner |
| 2014/0034497 A1 | 2/2014 | Davis |
| 2014/0296083 A1 | 10/2014 | Brown |
| 2014/0329693 A1 | 11/2014 | Reid |
| 2014/0346059 A1 | 11/2014 | Akeson |
| 2015/0060276 A1 | 3/2015 | Golovchenko |

FOREIGN PATENT DOCUMENTS

| | | |
|---|---|---|
| EP | 1236807 | 9/2002 |
| EP | 1712891 | 10/2006 |
| JP | 2004205495 | 7/2004 |
| JP | 2004333485 | 11/2004 |
| JP | 2005538377 | 12/2005 |
| JP | 2008507703 | 3/2008 |
| JP | 2010502936 | 1/2010 |
| JP | 2010524436 | 7/2010 |
| JP | 2011506994 | 3/2011 |
| JP | 2012026986 | 2/2012 |
| JP | 2013512447 | 4/2013 |
| WO | WO-9106678 | 5/1991 |
| WO | WO-9321340 | 10/1993 |
| WO | WO-9732999 | 9/1997 |
| WO | WO-9746704 | 12/1997 |
| WO | WO-2002022883 | 3/2002 |
| WO | WO-2002029003 | 4/2002 |
| WO | WO-02079519 | 10/2002 |
| WO | WO-03095617 | 11/2003 |
| WO | WO-2004007773 | 1/2004 |
| WO | WO-2004055160 | 7/2004 |
| WO | WO-2005084367 | 9/2005 |
| WO | WO-2006020775 | 2/2006 |
| WO | WO-2007002204 | 1/2007 |
| WO | WO-2007053702 | 5/2007 |
| WO | WO-2007053719 | 5/2007 |
| WO | WO-2007062105 | 5/2007 |
| WO | WO-2007115694 | 10/2007 |
| WO | WO-2007127327 | 11/2007 |
| WO | WO-2007146158 | 12/2007 |
| WO | WO-2008034602 | 3/2008 |
| WO | WO-2008069973 | 6/2008 |
| WO | WO-2008071982 | 6/2008 |
| WO | WO-2008079169 | 7/2008 |
| WO | WO-2008102120 | 8/2008 |
| WO | WO-2008124107 | 10/2008 |
| WO | WO-2009005547 | 1/2009 |
| WO | WO-2009047703 | 4/2009 |
| WO | WO-2009051807 | 4/2009 |
| WO | WO-2009077734 | 6/2009 |
| WO | WO-2009138760 | 11/2009 |
| WO | WO-2010044932 | 4/2010 |
| WO | WO-2010122293 | 10/2010 |
| WO | WO-2011097028 | 8/2011 |
| WO | WO-2011103424 | 8/2011 |
| WO | WO-2011106459 | 9/2011 |
| WO | WO-2012009578 | 1/2012 |
| WO | WO-2012088339 | 6/2012 |
| WO | WO-2012088341 | 6/2012 |
| WO | WO-2012121756 | 9/2012 |
| WO | WO-2013011879 | 1/2013 |
| WO | WO-2013082619 | 6/2013 |

(56) References Cited

FOREIGN PATENT DOCUMENTS

OTHER PUBLICATIONS

Aksimentiev, et al. Microscopic Kinetics of DNA Translocation through synthetic nanopores. Biophys J. Sep. 2004;87(3):2086-97.
Anderson, Olaf Sparre. "Sequencing and the single channel." Biophysical journal 77.6 (1999): 2899.
Ashkenasy, et al. Recognizing a single base in an individual DNA strand: a step toward DNA sequencing in nanopores. Angew Chem Int Ed Engl. Feb. 18, 2005:44(9):1401-4.
Atanasov, et al. Membrane on a chip: a functional tethered lipid bilayer membrane on silicon oxide surfaces. Biophys J. Sep. 2005;89(3):1780-8.
Baaken, et al. Planar microelectrode-cavity array for high-resolution and parallel electrical recording of membrane ionic currents. Lab Chip. Jun. 2008;8(6):938-44. Epub Apr. 16, 2008.
Bai, et al. Design and synthesis of a photocleavable biotinylated nucleotide for DNA analysis by mass spectrometry. Nucleic Acids Res. Jan. 26, 2004;32(2):535-41. Print 2004.
Benner et al., "Sequence-specific detection of individual DNA polymerase complexes in real time using a nanopore," Nature Nanotechnology (Nov. 2007), pp. 718-724, vol. 2.
Bezrukov, et al. Counting polymers moving through a single ion channel. Nature. Jul. 28, 1994;370(6487):279-81.
Bezrukov, et al. Dynamic partitioning of neutral polymers into a single ion channel. In NATO Advanced Research Workshop: Structure and dynamics of confined polymers. Kulwer Press. 2002; 117-130.
Bezrukov, et al. Dynamics and free energy of polymers partitioning into a nanoscale pore. Macromolecules. 1996; 29:8517-8522.
Bezrukov, et al. Neutral polymers in the nanopores of alamethicin and alpha-hemolysin. Biologicheskie Membrany 2001, 18, 451-455.
Boireau, et al. Unique supramolecular assembly of a redox protein with nucleic acids onto hybrid bilayer: towards a dynamic DNA chip. Biosens Bioelectron. Feb. 15, 2005;20(8):1631-7.
Bokhari, et al. A parallel graph decomposition algorithm for DNA sequencing with nanopores. Bioinformatics. Apr. 1, 2005;21(7):889-96. Epub Nov. 11, 2004.
Buchmann, et al. Electrochemical release from gold-thiolate electrodes for controlled insertion of ion channels into bilayer membranes. Bioorg Med Chem. Mar. 15, 2004;12(6):1315-24.
Butler et al. Determination of RNA orientation during translocation through a biological nanopore. Biophys J. Jan. 1, 2006;90(1):190-9. Epub Oct. 7, 2005.
Butler et al. Single-molecule DNA detection with an engineered MspA protein nanopore. Proc Natl Acad Sci U S A. Dec. 30, 2008;105(52):20647-52. Epub Dec. 19, 2008.
Butler, et al. Ionic current blockades from DNA and RNA molecules in the alphahemolysis nanopore. Biophys J. Nov. 1, 2007;93(9):3229-40. Epub Aug. 3, 2007.
Chandler, et al. Membrane surface dynamics of DNA-threaded nanopores revealed by simultaneous single-molecule optical and ensemble electrical recording. Langmuir. Feb. 3, 2004;20(3):898-905.
Churbanov, et al. Duration learning for analysis of nanopore ionic current blockades. BMC Bioinformatics. Nov. 1, 2007;8 Suppl 7:S14.
Clarke, et al. Continuous base identification for single-molucule nanpore DNA sequencing. Nat Nanotechnol. Apr. 2009;4(4):265-70. Epub Feb. 22, 2009.
Cockroft, et al. A single-molecule nanpore device detects DNA polymerase activity with single-nucleotide resolution. J am Chem Soc. Jan. 23, 2008;130(3):818-20. Epub Jan. 1, 2008.
Danelon, et al. Cell membranes suspended across nanoaperture arrays. Langmuir. Jan. 3, 2006;22(1):22-5.
Deamer, et al. Characterization of nucleic acids by nanopore analysis. Acc Chem Res. Oct. 2002;35(10):817-25.

Derrington, et al. Nanopore DNA sequencing with MspA. Proc Natl Acad Sci U S A. Sep. 14, 2010;107(37):16060-5. Epub Aug. 26, 2010.
Einstein. Investigations on the theory of Brownian movement. Dover, New York. 1956.
Ervin, et al. Simultaneous alternating and direct current readout of protein ion channel blocking events using glass nanopore membranes. Anal Chem. Mar. 15, 2008;80(6):2069-76. Epub Feb. 23, 2008.
Flusberg, et al. Direct detection of DNA methylation during single-molecule, real-time sequencing. Nat Methods. Jun. 2010;7(6):461-5. Epub May 9, 2010.
Fologea, et al. Detecting single stranded DNA with a solid state nanopore. Nano Lett. Oct. 2005;5(10):1905-9.
Fologea, et al. Slowing DNA translocation in a solid-state nanopore. Nano Lett. Sep. 2005;5(9):1734-7.
Gu, et al. Stochastic sensing of organic analytes by a pore-forming protein containing a molecular adapter. Nature. Apr. 22, 1999;398(6729):686-90.
Haas, et al. Improvement of the quality of self assembled bilayer lipid membranes by using a negative potential. Bioelectrochemistry. Aug. 2001;54(1):1-10.
Halverson, et al. Anthrax biosensor, protective antigen ion channel asymmetric blockade. J Biol Chem. Oct. 7, 2005;280(40):34056-62. Epub Aug. 8, 2005.
Harlepp, et al. Probing complex RNA structures by mechanical force. Eur Phys J E Soft Matter. Dec. 2003;12(4):605-15.
Heins, et al. Detecting single porphyrin molecules in a conically shaped synthetic nanopore. Nano Lett. Sep. 2005;5(9):1824-9.
Heng, et al. Stretching DNA using the electric field in a synthetic nanopore. Nano Lett. Oct. 2005;5(10):1883-8.
Heng, et al. The electromechanics of DNA in a synthetic nanopore. Biophys J. Feb. 1, 2006;90(3)1098-106. Epub Nov. 11, 2005.
Henrickson, et al. Driven DNA transport into an asymmetric nanometer-scale pore. Phys Rev Lett. Oct. 2, 2000;85(14):3057-60.
Henrickson, et al. Probing single nanometer-scale pores with polymeric molecular rulers. J Chem Phys. Apr. 7, 2010;132(13):135101. doi: 10.1063/1.3328875.
Holden, et al. Direct introduction of single protein channels and pores into lipid bilayers. J Am Chem Soc. May 11, 2005;127(18):6502-3.
Holden, et al. Direct transfer of membrane proteins from bacteria to planar bilayers for rapid screening by single-channel recording. Nat Chem Biol. Jun. 2006;2(6):314-8. Epub May 7, 2006.
Hromada, et al. Single molecule measurements within individual membrane-bound ion channels using a polymer-based bilayer lipid membrane chip. Lab Chip. Apr. 2008;8(4):602-8. Epub Feb. 29, 2008.
International Preliminary Report on Patentability dated Dec. 24, 2008 in connection with International Application No. PCT/US2007/013559.
International Search Report and Written Opinion dated Aug. 28, 2012 for PCT/US2011/066627.
International Search Report and Written Opinion dated Aug. 28, 2012 for PCT/US2011/066632.
International Search Report and Written Opinion dated Jun. 2, 2013 for PCT/US2013/022273.
International Search Report and Written Opinion dated Mar. 18, 2013 for PCT/US2012/063099.
International Search Report and Written Opinion dated May 16, 2013 for PCT/US2013/026514.
International Search Report and Written Opinion dated May 3, 2012 for PCT/US2012/020827.
International Search Report and Written Opinion dated May 9, 2013 for PCT/US2013/028058.
International Search Report and Written Opinion dated Nov. 5, 2012 for PCT/US2011/064490.
International Search Report and Written Opinion dated Oct. 29, 2007 for PCT/US2007/013559.
International Search Report dated Feb. 24, 2013 for PCT/US2011/065640.

(56) References Cited

OTHER PUBLICATIONS

Ito, et al. Simultaneous determination of the size and surface charge of individual nanoparticles using a carbon nanotube-based Coulter counter. Anal Chem. May 15, 2003;75(10):2399-406.
Jetha et al. Forming an α-Hemolysin Nanopore for Single-Molecule Analysis. Micro and Nano Technologies in Bioanalysis. Humana Press, 2009. 113-127.
Jiang et al. Passive and Electrically Actuated Solid-State Nanopores for Sensing and Manipulating DNA.€Nanopore-Based Technology. Humana Press, 2012. 241-264.
Ju, et al. Cassette labeling for facile construction of energy transfer fluorescent primers. Nucleic Acids Res. Mar. 15, 1996;24(6):1144-8.
Ju, et al. Energy transfer primers: a new fluorescence labeling paradigm for DNA sequencing and analysis. Nat Med. Feb. 1996;2(2):246-9.
Ju, et al. Fluorescence energy transfer dye-labeled primers for DNA sequencing and analysis. Proc Natl Acad Sci U S A. May 9, 1995;92(10):4347-51.
Ju, et al. Four-color DNA sequencing by synthesis using cleavable fluorescent nucleotide reversible terminators. Proc Natl Acad Sci U S A. Dec. 26, 2006;103(52):19635-40. Epub Dec. 14, 2006.
Jurak, et al. Wettability and topography of phospholipid DPPC multilayers deposited by spin-coating on glass, silicon and mica slides. Langmuir. Sep. 25, 2007;23(20):10156-63. Epub Aug. 28, 2007.
Kang, et al. A storable encapsulated bilayer chip containing a single protein nanopore. J Am Chem Soc. Apr. 18, 2007;129(15):4701-5. Epub Mar. 22, 2007.
Kasianowicz, et al. Characterization of individual polynucleotide molecules using a membrane channel. Proc Natl Acad Sci U S A. Nov. 26, 1996;93(24)13770-3.
Kasianowicz, et al. Physics of DNA threading through a nanometer pore and applications to simultaneous multianalyte sesnsing. In NATO Advanced Research Workshop: Structure and dynamics of confined polymers. Kluwer Press. 2002; 141-163.
Kasianowicz, et al. Simultaneous multianalysis detection with a nanopore. Anal. Chem. 2001; 73:2268-2272.
Kasianowicz. Nanometer-scale pores: potential applications for analyte detection and DNA characterization. Dis Markers. 2002;18(4):185-91.
Kasianowicz. Nanopores: flossing with DNA. Nat Mater. Jun. 2004;3(6):355-6.
Kawano, et al. Controlling the translocation of single-stranded DNA through alphahemolysin ion channels using viscosity. Langmuir. Jan. 20, 2009;25(2)1233-7.
Kim et al. Rapid fabrication of uniformly sized nanopores and nanopore arrays for parallel DNA analysis.€Advanced Materials€18. 23 (2006): 3149-3153.
Krasilnikov, et al. A simple method for the determination of the pore radius of ion channels in planar lipid bilayer membranes. FEMS Microbiol Immunol. Sep. 1992;5(1-3):93-100.
Krasilnikov, et al. Single polymer molecules in a protein nanopore in the limit of a strong polymer-pore attraction. Phys Rev Lett. Jul. 7, 2006;97(1):018301. Epub Jul. 5, 2006.
Krasilnikov, et al. Sizing channels with neutral polymers. In NATO Advanced Research Workshop: Structure and dynamics of confined polymers. Kluwer Press. 2002; 97-116.
Kullman, et al. Transport of maltodextrins through maltoporin: a single-channel study. Biophys J. Feb. 2002;82(2):803-12.
Kutik, et al. Dissecting membrane insertion of mitochondrial beta-barrel proteins. Cell. Mar. 21, 2008;132(6):1011-24.
Lee, et al. Enhancing the catalytic repertoire of nucleic acids: a systematic study of linker length and rigidity. Nucleic Acids Res. Apr. 1, 2001;29(7)1 565-73.
Li, et al. A photocleavable fluorescent nucleotide for DNA sequencing and analysis. Proc Natl Acad Sci U S A. Jan. 21, 2003;100(2):414-9. Epub Jan. 6, 2003.
Li, et al. Ion-beam sculpting at nanometre length scales. Nature. Jul. 12, 2001;412(6843)166-9.

Linear Technology, High Efficiency Thermoelectric Cooler Controller, 2001.
Low Noise, Dual Switched Integrator, Burr-Brown Corporation, Sep. 1994.
Lundquist, et al. A new tri-orthogonal strategy for peptide cyclization. Org Lett. Sep. 19, 2002;4(19):3219-21.
Madampage, et al. Nanopore detection of antibody prion interactions. Anal Biochem. Jan. 1, 2010;396(1):36-41. Epub Aug. 21, 2009.
Mager et al., "Lipid bilayer deposition and patterning via air bubble collapse." Langmuir 23.18 (2007): 9369-9377.
Mathe, et al. Nanopore unzipping of individual DNA hairpin molecules. Biophys J. Nov. 2004;87(5):3205-12. Epub Sep. 3, 2004.
Mathe, et al. Orientation discrimination of single-stranded DNA inside the alpha-hemolysin membrane channel. Proc Natl Acad Sci U S A. Aug. 30, 2005;102(35):12377-82. Epub Aug. 19, 2005.
Maurer, et al. Reconstitution of ion channels in agarose-supported silicon orifices. Biosens Bioelectron. May 15, 2007;22(11):2577-84. Epub Nov. 13, 2006.
McNally, et al. Optical recognition of converted DNA nucleotides for single-molecule DNA sequencing using nanopore arrays. Nano Lett. Jun. 9, 2010;10(6):2237-44.
Meller, et al. Rapid nanopore discrimination between single polynucleotide molecules. Proc Natl Acad Sci U S A. Feb. 1, 2000;97(3)1079-84.
Meller, et al. Single molecule measurements of DNA transport through a nanopore. Electrophoresis. Aug. 2002;23(16):2583-91.
Mohammad, et al. Controlling a single protein in a nanopore through electrostatic traps. J Am Chem Soc. Mar. 26, 2008;130(12)4081-8. Epub Mar. 6, 2008.
Mollazadeh et al. "Micropower CMOS integrated low-noise amplification, filtering, and digitization of multimodal neuropotentials." Biomedical Circuits and Systems, IEEE Transactions on 3.1 (2009): 1-10.
Molloy et al. "Automation of biochip array technology for quality results." Clinical Chemical Laboratory Medicine 43.12 (2005): 1303-1313.
Mosquera et al. Thermal decomposition and fractal properties of sputter-deposited platinum oxide thin films.€Journal of Materials Research27.05 (2012): 829-836.
Movileanu, et al. Partitioning of a polymer into a nanoscopic protein pore obeys a simple scaling law. Proc Natl Acad Sci U S A. Aug. 28, 2001;98(18)10137-41. Epub Aug. 14, 2001.
Movileanu, et al. Partitioning of individual flexible polymers into a nanoscopic protein pore. Biophys J. Aug. 2003;85(2):897-910.
Nakane et al. "Nanopore sensors for nucleic acid analysis." Journal of Physics: Condensed Matter 15.32 (2003): R1365.
Nakane, et al. A Nanosensor for Transmembrane Capture and Identification of Single Nucleic Acid Molecules, Biophysical Journal, vol. 87, Issue 1, Jul. 2004, pp. 615-621, ISSN 0006-3495.
Office action dated Feb. 25, 2013 for U.S. Appl. No. 13/396,522.
Office action dated Apr. 11, 2013 for U.S. Appl. No. 12/658,603.
Office action dated Apr. 26, 2012 for U.S. Appl. No. 12/658,591.
Office action dated Apr. 26, 2012 for U.S. Appl. No. 12/658,601.
Office action dated Jun. 15, 2012 for U.S. Appl. No. 12/658,604.
Office action dated Jun. 28, 2012 for U.S. Appl. No. 12/308,091.
Office action dated Aug. 3, 2012 for U.S. Appl. No. 12/658,602.
Office action dated Oct. 02, 2012 for U.S. Appl. No. 12/658,603.
Office action dated Oct. 16, 2012 for U.S. Appl. No. 12/658,601.
Office action dated Oct. 25, 2012 for U.S. Appl. No. 12/658,591.
Office action dated Nov. 29, 2011 for U.S. Appl. No. 12/308,091.
Office action dated Dec. 17, 2012 for U.S. Appl. No. 13/620,973.
Osaki et al. Analytical Chemistry, Multichannel Simultaneous Measurements of Single-Molecule Translocation in a-Hemolysin Nanopore Array, 2009, 81, pp. 9866-9870.
Oxford Nanopore Technologies, Sensor Array Chip, Jul. 14, 2011.
Park, et al. DNA hybridization sensors based on electrochemical impedance spectroscopy as a detection tool. Sensors (Basel). 2009;9(12):9513-32. Epub Nov. 26, 2009.
Perkins, et al. Relaxation of a single DNA molecule observed by optical microscopy. Science. May 6, 1994;264(5160):822-6.
Pourmand, et al. Multiplex Pyrosequencing. Acids Res. Apr. 1, 2002;30(7):e31.

(56) References Cited

OTHER PUBLICATIONS

Purnell, et al. Discrimination of single base substitutions in a DNA strand immobilized in a biological nanopore. ACS Nano. Sep. 22, 2009;3(9):2533-8.
Reiner, et al. Temperature sculpting in yoctoliter volumes. J Am Chem Soc. Feb. 27, 2013;135(8):3087-94. doi: 10.1021/ja309892e. Epub Feb. 14, 2013.
Reiner, et al. Theory for polymer analysis using nanopore-based single-molecule mass spectrometry. Proc Natl Acad Sci USA. Jul. 6, 2010;107(27):12080-5. doi: 10.1073/pnas.1002194107. Epub Jun. 21, 2010.
Rief, et al. Sequence-dependent mechanics of single DNA molecules. Nat Struct Biol. Apr. 1996;6(4):346-9.
Robertson, et al. Single-molecule mass spectrometry in solution using a solitary nanopore. Proc Natl Acad Sci U S A. May 15, 2007;104(20):8207-11. Epub May 9, 2007.
Rosenblum, et al. New dye-labeled terminators for improved DNA sequencing patterns. Nucleic Acids Res. Nov. 15, 1997;25(22):4500-4.
Rosentein et al. "Nanopore DNA sensors in CMOS with on-chip low-noise preamplifiers." Solid-State Sensors, Actuators and Microsystems Conference (TRANSDUCERS), 2011 16th International. IEEE, 2011.
Rostovtsev, et al. A stepwise huisgen cycloaddition process: copper(I)-catalyzed regioselective "ligation" of azides and terminal alkynes. Angew Chem Int Ed Engl. Jul. 15, 2002;41(14):2596-9.
Rotem et al., Temperature Measurement in the Intel Core Duo Processor, 2007.
Saleh, et al. Direct detection of antibody-antigen binding using an on-chip artificial pore. Proc Natl Acad Sci U S A. Feb. 4, 2003;100(3):820-4. Epub Jan. 27, 2003.
Sanchez-Magraner, et al. Membrane insertion of *Escherichia coli* alphahemolysin is independent from membrane lysis. J Biol Chem. Mar. 3, 2006;281(9):5461-7. Epub Dec. 22, 2005.
Sauer-Budge, et al. Unzipping kinetics of double-stranded DNA in a nanopore. Phys Rev Lett. Jun. 13, 2003;90(23):238101. Epub Jun. 9, 2003.
Schneider et al. "DNA sequencing with nanopores."Nature biotechnology€30.4 (2012): 326-328.
Schuster et al., Self-Assembled a-Hemolysin Pores in an S-Layer-Supported Lipid Bilayer, Biochimica et Biophysica Acta 1370, (1998) 280-288.
Seo, et al. Photocleavable fluorescent nucleotides for DNA sequencing on a chip constructed by site-specific coupling chemistry. Proc Natl Acad Sci U S A. Apr. 13, 2004;101(15):5488-93. Epub Apr. 2, 2004.
Shim, et al. Encapsulating a single G-quadruplex aptamer in a protein nanocavity. J Phys Chem B. Jul. 17, 2008;112(28):8354-60. Epub Jun. 19, 2008.
Simon, et al. Formation and stability of a suspended biomimetic lipid bilayer on silicon submicrometer-sized pores. J Colliod Interface Sci. Apr. 15, 2007;308(2):337-43. Epub Jan. 31, 2007.
Singer et al., Nanopore Based Sequence Specific Detection of Duplex DNA for Genomic Profiling, Jan. 8, 2010, published Jan. 20, 2010, pp. 738-743.
Singh, et al. Synthesis of natural flutimide and analogous fully substituted pyrazine-2,6-diones, endonuclease inhibitors of influenza virus. J Org Chem. Aug. 10, 2001;66(16):5504-16.
Smith, et al. Overstretching B-DNA: the elastic response of individual double-stranded and single-stranded DNA molecules. Science. Feb. 9, 1996;271(5250):795-9.
Stanford, et al. Transport of DNA through a single nanometer-scale pore: evolution of signal structure. IEEE Workshop on Genomic Signal Processing and Statistics. Baltimore, MD. May 26, 2004.
Stanford, et al. Using HMMs to Quantify Signals from DNA Driven Through a Nanometer-Scale Pore. IEEE Workshop on Genomic Signal Processing and Statistics. Raleigh, NC. Oct. 2002; 11-13.
Stefureac, et al. Nanopore analysis of the interaction of metal ions with prion proteins and peptides. Biochem Cell Biol. Apr. 2010;88(2):347-58.
Stefureac, et al. Transport of alpha-helical peptides through alpha-hemolysin and aerolysis pores. Biochemistry. Aug. 1, 2006;45(30):9172-9.
Stoddart, et al. Nucleobase recognition in ssDNA at the central constriction of the alpha-hemolysin pore. Nano Lett. Sep. 8, 2010;10(9):3633-7.
Stoddart, et al. Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.
Storm, et al. Translocation of double-strand DNA through a silicon oxide nanopore. Phys Rev E Stat Nonlin Soft Matter Phys. May 2005;71(5 Pt 1):051903. Epub May 6, 2005.
Streater, et al. Novel 3-hydroxy-2(1 H)-pyridinones. Synthesis, iron(III)-chelating properties, and biological activity. J Med Chem. Jun. 1990;33(6):1749-55.
Studer, et al. Formation of individual protein channels in lipid bilayers suspended in nanopores. Colloids Surf B Biointerfaces. Oct. 15, 2009;73(2):325-31. Epub Jun. 10, 2009.
Suzuki, et al. Highly reproducible method of planar lipid bilayer reconstitution in polymethyl methacrylate chip. Langmuir. Feb. 14, 2006;22(4):1937-42.
Thei et al., Parallel Recording of Single Ion Channels: A Heterogeneous System Approach, IEEE Transactions on Nanotechnology, vol. 9, No. 3, May 2010.
Thomson et al. Preliminary nanopore cheminformatics analysis of aptamer-target binding strength. BMC Bioinformatics. Nov. 1, 2007;8 Suppl 7:S11.
Timp et al. "Nanopore sequencing: electrical measurements of the code of life." Nanotechnology, IEEE Transactions on 9.3 (2010): 281-294.
U.S. Appl. No. 61/170,729, filed Apr. 20, 2009.
UK search and examination report dated Feb. 25, 2013 for GB Application No. 1216656.7.
UK search and examination report dated May 1, 2013 for GB Application No. 1216026.3.
Venkatesan et al. "Nanopore sensors for nucleic acid analysis." Nature nanotechnology 6.10 (2011): 615-624.
Vercoutere et al., "Discrimination among individual Watson-Crick base pairs at the termini of single DNA hairpin molecules," Nucleic Acids Research (2003), pp. 1311-1318, vol. 31.
Vercoutere et al., "Rapid discrimination among individual DNA hairpin molecules at single-nucleotide resolution using an ion channel," Nature Biotechnology (Mar. 2001) pp. 248-252, vol. 19.
Viasnoff, et al. Probing DNA base pairing energy profiles using a nanopore. Eur Biophys J. Feb. 2009;38(2):263-9. Epub Oct. 3, 2008.
Wang, et al. DNA heterogeneity and phosphorylation unveiled by single-molecule electrophoresis. Proc Natl Acad Sci U S A. Sep. 14, 2004;101(37):13472-7. Epub Sep. 1, 2004.
Wanunu, et al. DNA profiling using solid-state nanopores: detection of DNA-binding molecules. Nano Lett. Oct. 2009;9(10):3498-502.
Weng, et al. Fluid biomembranes supported on nanoporous aerogel/xerogel substrates. Langmuir. Aug. 17, 2004;20(17):7232-9.
Wilson, et al. Electronic control of DNA polymerase binding and unbinding to single DNA molecules. ACS Nan. Apr. 28, 2009;3(4):995-1003.
Wilson, et al. Feedback control of a DNA molecule tethered in a nanopore to repeatedly probe DNA-binding enzymes. Conf Proc IEEE Eng Med Biol Soc. 2008;2008:5745-8.
Winters-Hilt, et al. Nanopore-based kinetics analysis of individual antibody-channel and antibody-antigen interactions. BMC Bioinformatics. Nov. 1, 2007;8 Suppl 7:S20.
Woodside, et al. Direct measurement of the full, sequence-dependent folding landscape of a nucleic acid. Science. Nov. 10, 2006;314(5801):1001-4.
Woodside, et al. Nanomechanical measurements of the sequence-depepndent folding landscapes of single nucleic acid hairpins. Proc Natl Acad Sci U S A. Apr. 18, 2006;103(16):6190-5. Epub Apr. 10, 2006.
WP Thompson Letter May 28, 2013.

(56) References Cited

OTHER PUBLICATIONS

Wu, et al. Single-molecule detection of nitrogen mustards by covalent reaction within a protein nanopore. J Am Chem Soc. May 28, 2008;130(21):6813-9. Epub Apr. 30, 2008.
Zeineldin, et al. Using bicellar mixtures to form supported and suspended lipid bilayers on silicon chips. Langmuir. Sep. 12, 2006;22(19):8163-8.
Zwolak, et al. Electronic signature of DNA nucleotides via transverse transport. Nano Letters. Mar. 2005;5(3):421-4.
Chen et al., Probing Single DNA Molecule Transport using Fabricated Nanopores, (Nano Lett, 2004, 4(11), pp. 2293-2298).
Axopatch 2008 Patch Clamp Theory and Operation, Mar. 1999 (Year: 1999).
Jiang et al. "Fabrication of sponge-like nanoporous platinum electrocatalysts for oxygen reduction through alloying and dealloying processes." Journal of University of Science and Technology of China. Jun. 30, 2008. vol. 38 No. 5. pp. 614-622.
Kumar, et al. PEG-labeled nucleotides and nanopore detection for single molecule DNA sequencing by synthesis. Sci Rep. 2012;2:684. Epub Sep. 21, 2012.
Wang et al., An Intergrated, Low Noise Patch-Clamp Amplifier for Biological Nanopore Applications, 32nd Annual International Conference of IEEE EMBS, Buenos Aires, Argentina Aug. 31-Sep. 4, 2010.

\* cited by examiner

SYSTEM FOR DETECTING ELECTRICAL PROPERTIES OF A MOLECULAR COMPLEX

CROSS REFERENCE TO OTHER APPLICATIONS

This application is a continuation of co-pending U.S. patent application Ser. No. 14/558,268, entitled SYSTEM FOR DETECTING ELECTRICAL PROPERTIES OF A MOLECULAR COMPLEX, filed Dec. 2, 2014, which is a continuation of U.S. patent application Ser. No. 13/272,128, now U.S. Pat. No. 8,962,242, entitled SYSTEM FOR DETECTING ELECTRICAL PROPERTIES OF A MOLECULAR COMPLEX, filed Oct. 12, 2011, which claims priority to U.S. Provisional Patent Application No. 61/435,700, entitled SYSTEM FOR COMMUNICATING INFORMATION FROM AN ARRAY OF SENSORS, filed Jan. 24, 2011, all of which are incorporated herein by reference for all purposes.

BACKGROUND OF THE INVENTION

Advances in micro-miniaturization within the semiconductor industry in recent years have enabled biotechnologists to begin packing their traditionally bulky sensing tools into smaller and smaller form factors, onto so-called biochips. It would be desirable to develop techniques for biochips.

BRIEF DESCRIPTION OF THE DRAWINGS

Various embodiments of the invention are disclosed in the following detailed description and the accompanying drawings.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

In various embodiments, the techniques described herein are implemented in a variety of systems or forms. In some embodiments, the techniques are implemented in hardware as an application-specific integrated circuit (ASIC) or a field-programmable gate array (FPGA). In some embodiments, a processor (e.g., an embedded one such as an ARM core) is used where the processor is provided or loaded with instructions to perform the techniques described herein. In some embodiments, the technique is implemented as a computer program product which is embodied in a computer readable storage medium and comprises computer instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Advances in micro-miniaturization within the semiconductor industry in recent years have enabled biotechnologists to begin packing their traditionally bulky sensing tools into smaller and smaller form factors, onto so-called biochips. These chips are essentially miniaturized laboratories that can perform hundreds or thousands of simultaneous biochemical reactions. Biochips enable researchers to quickly screen large numbers of biological analytes for a variety of purposes, from disease diagnosis to detection of bioterrorism agents.

Typically, a biochip includes a large array of cells. For example, a biochip for nucleotide sequencing may contain thousands or millions of single cells in an array. Each cell includes a molecular complex composed of monomers that make up an oligomeric nanopore and a single strand of DNA, and anything bound to that single strand of DNA. The nanopore is a small hole in an electrically insulating membrane that can be used as a single-molecule detector. A nanopore may be formed using a biological material, such as α-hemolysin or MspA. A nanopore may be formed using a solid-state material, such as a semiconductor material. When a small voltage is applied across a molecular complex containing a nanopore, an ionic current through the molecular complex can be measured to provide information about the structure of a molecule transiting the molecular complex. In a single cell of the array, an electrical circuit may be used for controlling the electrical stimulus applied across a lipid bilayer which contains a nanopore, and for detecting the electrical patterns, or signatures, of a molecule passing through the nanopore. These patterns or signatures identify events of interest such as additions or subtractions to the molecular complex, or conformational changes to the molecular complex. In order to reduce the cost of the array, physically small single cells with highly sensitive sensors therein are desirable.

Figure 1:
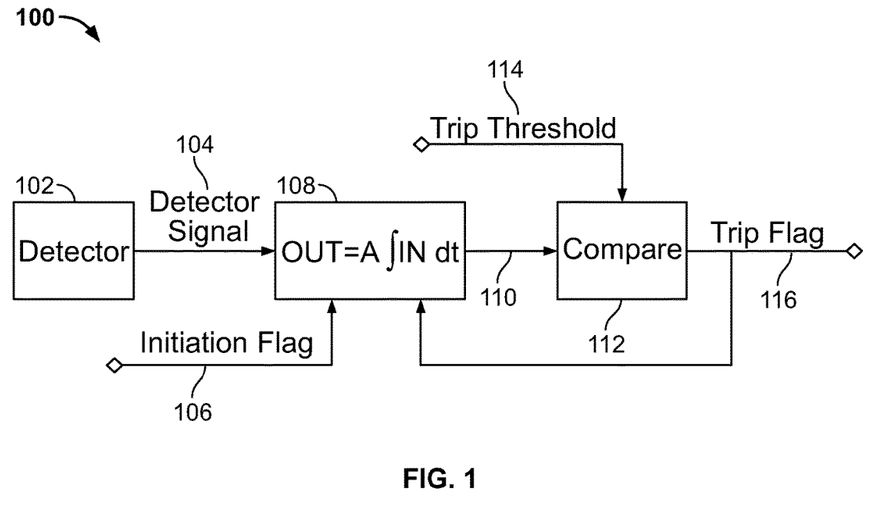
FIG. 1 is a block diagram illustrating an embodiment of a sensor circuit 100 for measuring a physical property within a single cell in a biochip.

FIG. 1 is a block diagram illustrating an embodiment of a sensor circuit 100 for measuring a physical property within a single cell in a biochip. As shown in FIG. 1, a physical property, e.g., a current, voltage, or charge, is detected by detector 102 as detected signal 104. Sensor circuit 100 may be used to measure the mean value of detected signal 104 without sampling as described further below.

In some embodiments, an initiation flag 106 resets an integrating amplifier 108 and starts a continuous integration of detected signal 104 over time. Integrated output 110 is compared with a trip threshold 114 using a comparator 112. When integrated output 110 reaches trip threshold 114, a trip flag 116 may be used as a feedback signal to integrating amplifier 108 for terminating the integration of detected signal 104. For example, when trip flag 116 is "on" or asserted, the integration is terminated. The duration of time between the assertion of initiation flag 106 and the assertion of trip flag 116 is proportional to the mean value of detected signal 104, e.g., the mean value of a current. Accordingly, the "on" and "off" of trip flag 116 (only 1 bit of information) may be sent from the cell to an external processor for calculating the mean value of detected signal 104. Alternatively, the "on/off" information may be sent from the cell to an external storage for delayed processing. For example, the clock cycles at which initiation flag 106 and trip flag 116 are respectively asserted may be recorded in an external storage. The number of clock cycles between the two asserted flags may then be used to determine the mean value of detected signal 104 at a later time.

In some embodiments, more accurate results may be obtained by integrating detected signal 104 over multiple integrating cycles. For example, the determined mean value of detected signal 104 may be further averaged over multiple integrating cycles. In some embodiments, initiation flag 106 is based at least in part on trip flag 116. For example, initiation flag 106 may be re-asserted in response to trip flag 116 being asserted. In this example, trip flag 116 is used as a feedback signal for reinitializing integrating amplifier 108, such that another cycle of integration of detected signal 104 may begin as soon as the previous cycle of integration is terminated. Re-asserting initiation flag 106 immediately after trip flag 116 is asserted reduces the portion of time when detector 102 generates a signal that is not integrated and thus not measured. The integration occurs over approximately the entire time that the signal is available. As a result, most of the information of the signal is captured, thereby minimizing the time to obtain an average value for the measured signal.

Shot noise may corrupt trip flag 116 during certain integrating cycles. Accordingly, some embodiments may include logic to determine whether trip flag 116 has been corrupted by shot noise in a particular integrating cycle before trip flag 116 is saved or used for any calculation.

Figure 2:
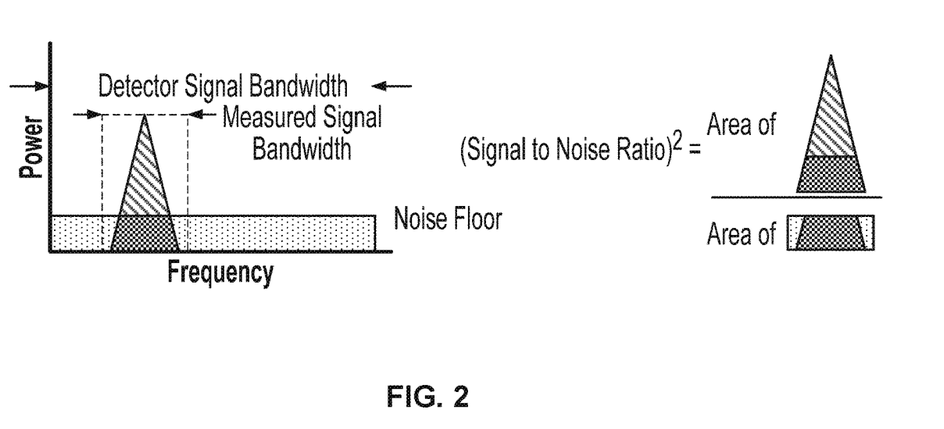
FIG. 2 illustrates that with a constant noise floor, as the measured signal bandwidth decreases, the signal to noise ratio increases, thereby improving the sensitivity of sensor circuit 100 of FIG. 1.

The sensitivity of sensor circuit 100 is maximized by continuously integrating detected signal 102 without sampling. This serves to limit the bandwidth of the measured signal. With continuous reference to FIG. 1, trip threshold 114 and an integration coefficient A set the bandwidth of the measured signal. As integration coefficient A decreases or as trip threshold 114 increases, the measured signal bandwidth decreases. FIG. 2 illustrates that with a constant noise floor, as the measured signal bandwidth decreases, the signal to noise ratio increases, improving the sensitivity of sensor circuit 100. In some embodiments, the measured signal bandwidth can be dynamically adjusted by varying the trip threshold 114.

Figure 3:
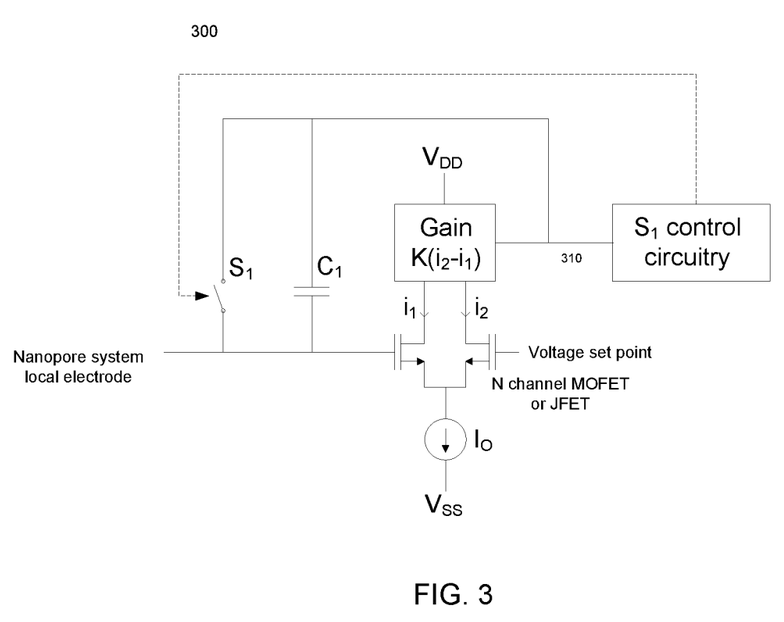
FIG. 3 is a circuit diagram illustrating an embodiment of a sensor circuit 300 for measuring a physical property, e.g., a current, within a single cell in a nanopore array.
Figure 4:
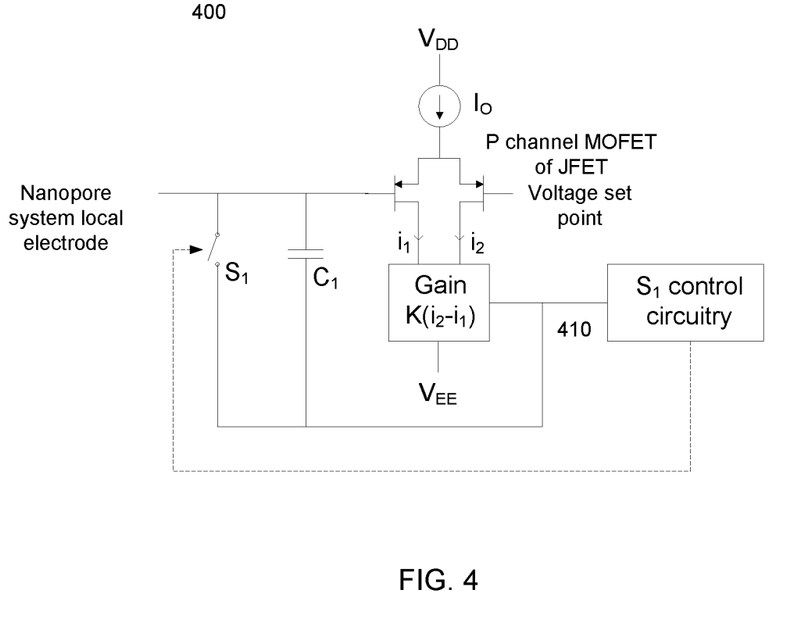
FIG. 4 is a circuit diagram illustrating a second embodiment of a sensor circuit 400 for measuring a physical property within a single cell in a nanopore array.

FIG. 3 is a circuit diagram illustrating an embodiment of a sensor circuit 300 for measuring a physical property, e.g., a voltage, within a single cell in a nanopore array. FIG. 4 is a circuit diagram illustrating a second embodiment of a sensor circuit 400 for measuring a physical property within a single cell in a nanopore array.

With reference to FIGS. 3 and 4, the Si control circuitry includes a comparator and other logic, e.g., logic for switching. The other components of circuit 300 (or circuit 400), including the differential pair, implement an integrating amplifier similar to that in FIG. 1. The input of circuit 300 (or circuit 400) is connected to a nanopore system local electrode.

Figure 5:
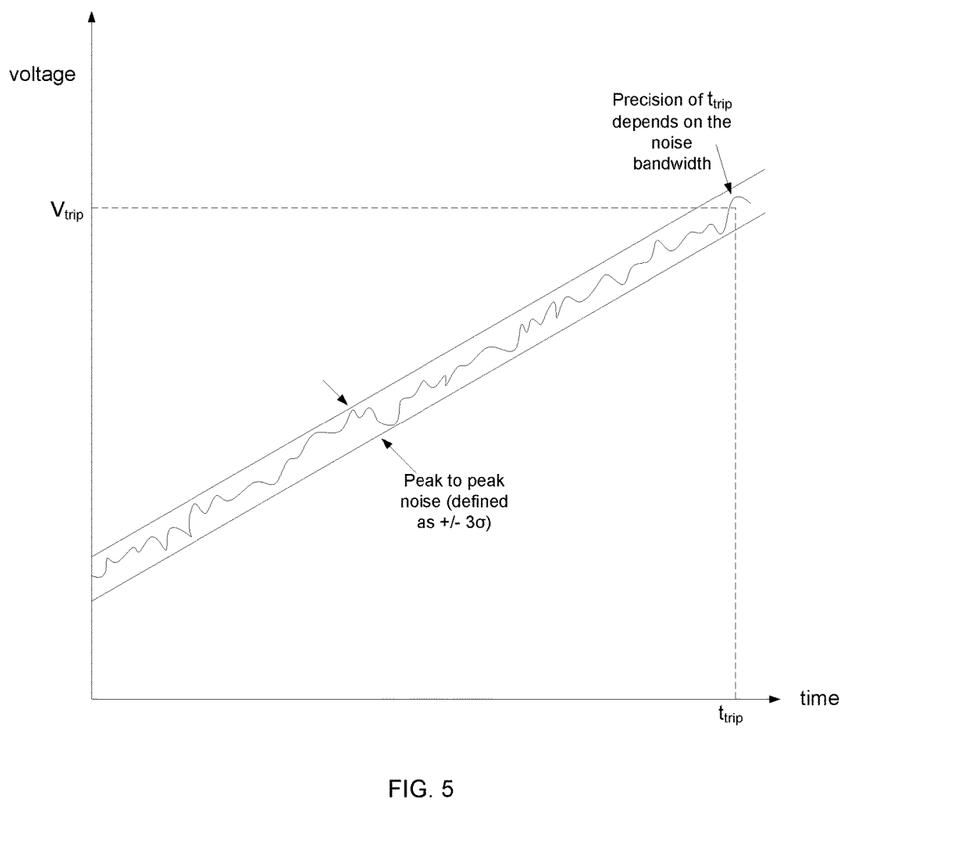
FIG. 5 is a diagram illustrating a plot of the voltage at the output of the integrating amplifier in circuit 300 or circuit 400 versus time.

FIG. 5 is a diagram illustrating a plot of the voltage at 310 (or 410) in circuit 300 (or circuit 400) versus time. In FIG. 5, $t_{trip}$ indicates the mean current flowing through a nanopore. Reducing the noise bandwidth reduces the noise associated with $t_{trip}$. Accordingly, the mean current measurement will have a higher signal to noise ratio (SNR) and be more precise.

The integrating amplifier generates signals within an expected bandwidth containing events of interest of the molecular complex. The integrating amplifier is configured to amplify only signals in the bandwidth of interest, and reject signals outside this bandwidth. Amplifying all signals amplifies mostly noise since the useful signal's bandwidth is much smaller than the detected signal, resulting in poor SNR. The bandwidth of interest may be limited by selecting appropriate values for $C_1$ and $I_O$ in circuits 300 and 400. In some embodiments, $C_1$ and $I_O$ are selected to limit the bandwidth of interest between 0.3 Hz and 300 Hz. In some embodiments, the bandwidth of interest can be dynamically adjusted by varying the values of $C_1$.

In some embodiments, trip flag 116 for each of the cells are further synchronized with a global clock shared by all the cells within the biochip. For example, trip flag 116 that is synchronized with a global clock may be generated by a pulse generation circuit. After synchronization, trip flag 116 is a single pulse that is in phase with the global clock.

Figure 6:
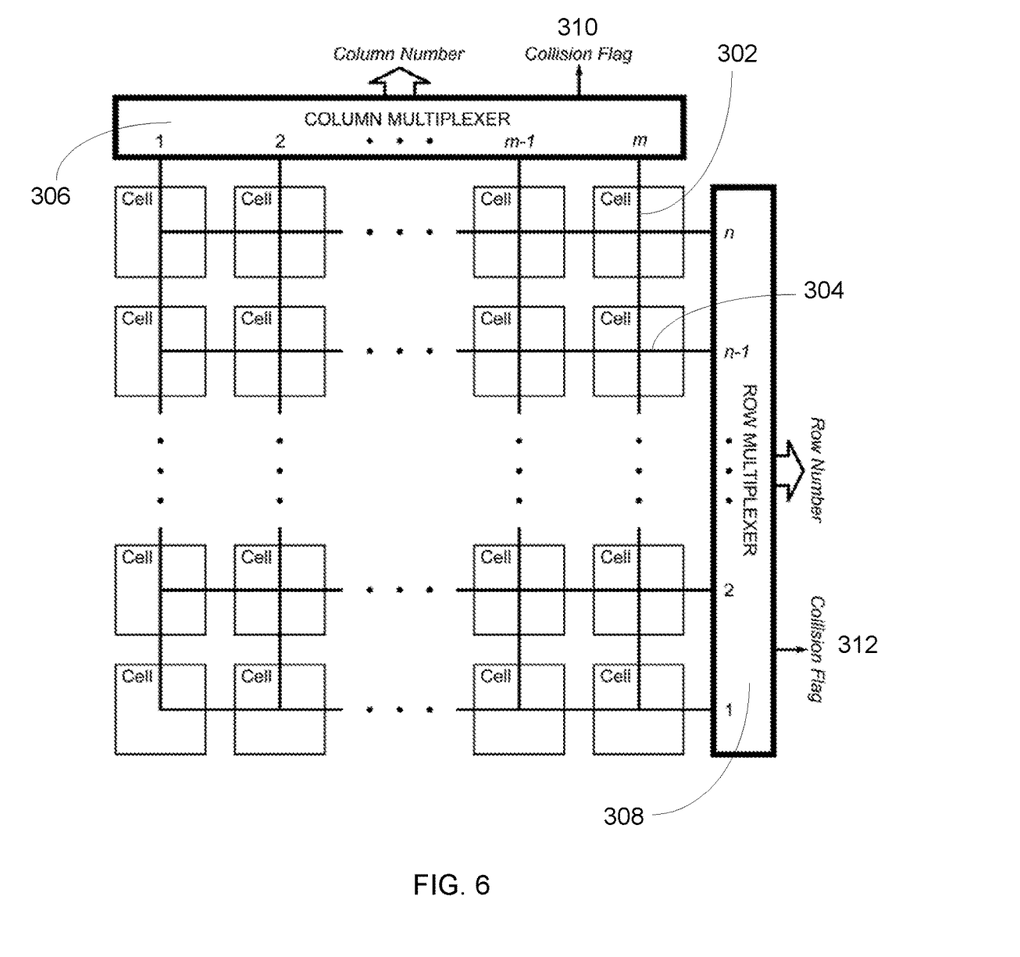
FIG. 6 is a block diagram illustrating an embodiment of a cell array in a biochip.

FIG. 6 is a block diagram illustrating an embodiment of a cell array in a biochip. Each of the cells may contain a sensor circuit 100 for measuring a physical property within the cell as described above. As shown in FIG. 6, the cell array has m columns by n rows of single cells. All the cells in a given column share the same column line 302, and all the cells in a given row share the same row line 304. When trip flag 116 for a particular cell is asserted, the cell asserts its particular column line 302 and row line 304. In order to reduce the pin count of the biochip, a column multiplexer 306 may be used to output a column number ($0$-$2^m$-$1$) to indicate which column line 302 has been asserted. Similarly, a row multiplexer 308 may be used to output a row number ($0$-$2^n$-$1$) to indicate which row line 304 has been asserted. For example, if trip flag 116 of the cell in the second column and the second row is asserted, the output column and row number is (1, 1). As long as only one cell asserts its trip flag 116 at a time, the reported column and row numbers are sufficient to uniquely identify which particular cell is asserted at a particular time.

The above techniques have a number of advantages over other approaches. The integrating amplifier requires minimal die area and allows for each array site to have its own dedicated measurement circuit. This feature removes the necessity of routing sensitive analog signals to the array periphery and avoids the need for multiplexing, thereby reducing noise. The integrating amplifier requires no pre-amplifier, sample and hold, or anti-aliasing filter, further reducing die area and potential error sources. Since only a single flag is required to denote the completion of a measurement, the integrating approach is an efficient way to communicate data from each array site. Measurements are being made continuously (other than the brief time required to reset the integration capacitor) so data is being gathered almost 100% of the time. Furthermore, each cell and its associated measurement circuit operate autonomously, allowing each cell to track the state of the molecule being measured. As described above, the integrating approach also has inherent signal averaging and noise advantages.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system for detecting electrical properties of a molecular complex, comprising:
   an electrode electrically coupled to a molecular complex that outputs an electrical signal affected by an electrical property of the molecular complex, wherein the effect of the electrical property of the molecular complex on the electrical signal is characterized by an expected bandwidth; and
   an integrating amplifier circuit configured to:
      receive the electrical signal from the electrode;
      selectively integrate the electrical signal within a predetermined bandwidth, wherein the predetermined bandwidth is selected at least in part based on the expected bandwidth;
      compare the selectively integrated electrical signal to a threshold;
      output an indication that the selectively integrated electrical signal has reached the threshold;
      initiate the integrating based on an initiation flag; and
      terminate the integrating based on the indication.

2. The system of claim 1, wherein the expected bandwidth comprises a bandwidth of events of interest of the molecular complex.

3. The system of claim 1, wherein the electrical property comprises one of the following: a current, voltage, charge, or capacitance.

4. The system of claim 1, wherein the integrating amplifier circuit is further configured to adjust the predetermined bandwidth based at least in part on adjusting the threshold.

5. The system of claim 1, wherein the indication corresponds to a mean value of the electrical property.

6. The system of claim 1, wherein the indication comprises a 1-bit flag.

7. The system of claim 1, wherein a time period between the initiating and the terminating of the integrating corresponds to a mean value of the electrical property.

8. The system of claim 1, wherein the integrating is repeated by deriving the initiation flag based at least in part on the indication.

9. The system of claim 8, wherein the initiation flag is re-asserted in response to the indication.

10. The system of claim 1, wherein the predetermined bandwidth is adjusted based at least in part on adjusting a capacitance value associated with a circuit performing the integrating.

11. The system of claim 1, wherein the predetermined bandwidth is adjusted based at least in part on adjusting a bias applied across a nanopore associated with the molecular complex.

12. The system of claim 1, wherein the integrating amplifier circuit is further configured to filter noise associated with the electrical signal.

* * * * *